United States Patent [19]

Suzukamo et al.

[11] Patent Number: 4,711,873

[45] Date of Patent: Dec. 8, 1987

[54] PROCESS FOR PREPARING SOLID BASE CATALYST

[75] Inventors: Gohfu Suzukamo, Ibaraki; Masami Fukao, Shiga; Masao Minobe, Niihama; Akemi Sakamoto, Takatsuki, all of Japan

[73] Assignee: Sumitomo Chemical Company, Limited, Osaka, Japan

[21] Appl. No.: 896,951

[22] Filed: Aug. 15, 1986

[30] Foreign Application Priority Data

Aug. 16, 1985 [JP] Japan ............................. 60-180869
Nov. 12, 1985 [JP] Japan ............................. 60-253568

[51] Int. Cl.$^4$ .......................... B01J 21/04; B01J 23/04
[52] U.S. Cl. ................................................. 502/344
[58] Field of Search ........................................ 502/344

[56] References Cited

U.S. PATENT DOCUMENTS 3,808,152  4/1974  Nagase et al. ..................... 502/346
3,897,509  7/1975  Nagase et al. ................. 260/666 PY

FOREIGN PATENT DOCUMENTS 769324  6/1971  Belgium .
1280134  11/1961  France .
2103221  4/1972  France .
2304594  10/1976  France .
1310900  3/1973  United Kingdom .

OTHER PUBLICATIONS

European Search Report, Application No. EP 86 11 1276, dtd. 1/6/87.

*Primary Examiner*—W. J. Shine
*Attorney, Agent, or Firm*—Birch, Stewart, Kolasch & Birch

[57] ABSTRACT

A solid base with improved properties, particularly excellent catalytic performance is prepared by reacting alumina and an alkali metal hydroxide at a temperature of from 200° to 500° C. and followed by reacting the resultant product with an alkali metal at a temperature of from 180° to 350° C. or reacting water-containing alumina and an alkali metal in such an amount that corresponds to a molar equivalent of water contained in alumina at a temperature in a range between a melting point of the alkali metal and 500° C. and then reacting the reaction product with an alkali metal at a temperature of from 180° to 350° C.

16 Claims, No Drawings

PROCESS FOR PREPARING SOLID BASE CATALYST

BACKGROUND OF THE INVENTION

1. Field of the Invention

The present invention relates to a process for preparing a solid base. More particularly, it relates to a process for preparing a solid base by reacting alumina, an alkali metal hydroxide and an alkali metal at a specific temperature or by reacting water-containing alumina and a alkali metal in a specific ratio at a specific temperature.

2. Description of the Prior Art

A solid base is useful as a catalyst used, for example, in isomerization of olefins, hydrogenation and dehydrogenation.

For example, an alkali metal dispersed on an anhydrous carrier with a large surface area (e.g., activated carbon, silica gel, alumina and the like) (cf. J. Am. Chem. Soc., 82, 387 (1960) is a known solid base catalyst. However, such a dispersion catalyst has unsatisfactory handleability and is unsafe since it ignites and loses its activity on contact with air. This is because the alkali metal is only finely dispersed on the carrier.

The present inventors have proposed a solid base which is prepared from alumina, an alkali metal hydroxide and an alkali metal or from water-containing alumina and an alkali metal. The solid base has a greater catalytic activity and a higher stability to air than the alkali metal dispersion catalyst (cf. Japanese Patent Publication Nos. 3274/1975 and 21378/1982).

SUMMARY OF THE INVENTION

One object of the present invention is to provide a solid base with improved handleability and catalytic performances.

Another object of the present invention is to provide a process for preparing a solid base with improved stability and performances formed from alumina, an alkali metal hydroxide and an alkali metal, or water-containing alumina and an alkali metal.

These and other objects are accomplished by a process for preparing a solid base according to the present invention which comprises reacting alumina and an alkali metal hydroxide at a temperature range of from 200° to 500° C. and then reacting the reaction product with an alkali metal at a temperature range of from 180° to 350° C., or by reacting water-containing alumina and an alkali metal in such an amount that corresponds to a molar equivalent of water contained in alumina at a temperature in a range between the melting point of the alkali metal and 500° C. and then reacting the reaction product with an alkali metal at a temperature range of from 180° to 350° C.

DETAILED DESCRIPTION OF THE INVENTION

The process of the present invention has been completed based on the finding that the catalyst performance of the solid base is influenced by preparation temperatures, namely, a temperature at which alumina, the alkali metal hydroxide and the alkali metal are reacted. Particularly, the alkali metal is reacted at a temperature at which water-containing alumina and the alkali metal are reacted, and more particularly, water-containing alumina is reacted with the excess portion of the alkali metal to the molar equivalent of water contained in alumina.

Examples of the alkali metal hydroxide are lithium hydroxide, sodium hydroxide, potassium hydroxide, rubidium hydroxide and cesium hydroxide and mixtures thereof. It may be used in a solid or liquid state.

As the alkali metal, an alkali metal of Group I of the Periodic Table such as sodium, potassium, rubidium and cesium is used. The alkali metals may be used as a mixture or as an alloy. Among the metals, sodium, potassium and alloys thereof are preferred.

As the combination of an alkali metal and an alkali metal hydroxide, a combination of an alkali metal and a hydroxide of other alkali metal, for example, combinations of potassium and sodium hydroxide, of sodium and potassium hydroxide or of sodium and lithium hydroxide can be used. However, more commonly used would be a combination of an alkali metal and its corresponding hydroxide, for example, a combination of sodium and sodium hydroxide, of potassium and potassium hydroxide and the like. From a practical approach, a combination of metal sodium and sodium hydroxide is used. Amounts of the alkali metal and the alkali metal hydroxide are 2 to 10% by weight and 5 to 40% by weight, respectively based on the weight of alumina in relation with the catalytic activity.

Usually, alumina with a relatively large surface area such as gamma-, chi-, rho- and eta-alumina is used. Alumina of 50 to 500 mesh, particularly, gamma-alumina of such mesh is preferred in view of the catalytic activity. Since alumina acts as a carrier as well as a reactant with the alkali metal and the alkali metal hydroxide, an alumina-containing compound such as kaolin and alumina silicate may be used in place of alumina, however, the use of alumina is preferred.

According to the present invention, alumina, the alkali metal and the alkali metal hydroxide are reacted at a specific temperature, as described above, to prepare the solid base with improved properties. As to the preferred sequence of the reactions, alumina and the alkali metal hydroxide are first reacted and followed by reacting the reaction product thereof with the alkali metal. Usually, the alkali metal hydroxide which is kept at a temperature that is higher than its melting point, is added to the alumina and reacted at a specific temperature, although an aqueous solution of the alkali metal hydroxide can be used in which the reaction mixture is heated to the specific temperature to carry out the reaction. The alkali metal is also added at a temperature higher than its melting point and reacted at a specific temperature, although it can be added in the form of a solution and heated to the specific temperature to carry out the reaction. The reactions are preferably carried out in an atmosphere of an inert gas such as nitrogen, helium and argon.

In the present invention, the properties of the prepared solid base are influenced by the reaction temperatures. Particularly, the catalytic activity of the solid base is greatly affected by the temperature at which the alkali metal is reacted.

Alumina and the alkali metal hydroxide are reacted at a temperature range of from 200° to 500° C., preferably from 250° to 450° C., and the alkali metal which is added to the reaction mixture at a temperature range of from 180° to 350° C., preferably from 200° to 330° C.

By reacting the compounds at such temperatures, the solid base prepared is characterized with a significantly high catalytic activity. Therefore, even in a small amount, the solid base of the present invention can effectively catalyze objective reactions.

The reaction time varies with other reaction conditions such as temperature. The reaction of alumina and the alkali metal hydroxide may be completed within 0.5 to 10 hours, and the subsequent reaction of the reaction product with the alkali metal may be completed within 10 to 300 minutes.

In addition to the above method, according to the present invention, the solid base can be prepared by reacting water-containing alumina with an alkali metal. This may be due to the formation of an alkali metal hydroxide from water contained in the alumina and the alkali metal. This method of preparation of the solid base will be illustrated hereinafter.

Various types of water-containing alumina can be used except for α-alumina.

Generally, alumina is produced by calcining aluminum hydroxide. According to the calcining temperature and time, alumina has various metastable states and a water content varies so that various type of alumina are produced. In the present invention, such alumina may be used. Preferably, water-containing alumina with a large surface area such as gamma-, chi-, rho- and eta-alumina are used.

Although it is rather difficult to measure the water content of alumina, the water content may be determined by weight loss upon heating during a heating period in which alumina in its original state is changed to α-alumina which contains no removable water. Usually, the water content of water-containing alumina is 1.3 to 10% by weight, preferably 2 to 7% by weight in terms of weight loss upon heating.

The alkali metal used in this preparation is the same as described above. A total amount of the alkali metal to be reacted is greater than the amount which corresponds to a molar equivalent of water contained in alumina. Preferably, 1.01 to 2 time molar equivalents of water contained in alumina.

According to the present invention, water-containing alumina is reacted with the alkali metal in at least such amount that corresponds to the molar equivalent of water contained in alumina, preferably in an atmosphere of an inert gas such as nitrogen, helium and argon, and then excess amount alkali metal is reacted with alumina. In this method, a type of alkali metal is first reacted and the type of alkali metal subsequently reacted may be the same or different.

Also in this second preparation of a solid base, the reaction temperatures, particularly, the reaction temperature in the second step, have significant influences on the properties of the solid base formed.

In the first reaction of water-containing alumina and alkali metal in an amount corresponding to the molar equivalent of contained water, a reaction temperature is in a range between the melting point of the alkali metal and 500° C. In the second reaction of alumina and excess alkali metal, a reaction temperature is from 180° to 350° C., preferably from 200° to 330° C. Preferably, the first reaction temperature and the second reaction temperature are substantially the same. In such a case, the reaction temperature is preferably from 180° to 350° C., more preferably from 200° to 330° C. In this case, the determined amount of the alkali metal can be added in one portion.

By reacting the compounds at such temperatures, a solid base having significantly high catalytic activity is prepared. Therefore, even in a small amount, the base of the present invention can effectively catalyze objective reactions.

The reaction time varies with other reaction conditions such as the reaction temperature. Usually, it is from 15 minutes to 10 hours.

Thus, the solid base prepared by the process of the present invention has a much higher catalytic activity than the conventional ones. Thus it can catalyze various reactions even in a small amount. The solid base of the present invention can be used to catalyze, for example, following reactions:

1. Isomerization of olefins
2. Dehydrogenation
3. Hydrogenation of unsaturated bonds
4. Condensation reactions Among these reactions, isomerization of olefins is significantly catalyzed by the solid base of the present invention. For example, isomerization of a terminal olefin to an internal olefin, particularly isomerization of an alkenyl bridged ring compound to a corresponding alkylidene bridged ring compound, is completed at room temperature or optionally at an elevated temperature in the presence of the solid base of the present invention.

Practically and presently preferred embodiments of the present invention will be illustrated by following examples.

EXAMPLE 1

To a 100 ml flask, gamma-alumina (31.9 g) was added and heated to 490°-500° C. under nitrogen with stirring at the same temperature for one hour. After cooling to 300°-310° C., sodium hydroxide (4.5 g) was added thereto and stirred at the same temperature for 3 hours.

Then, metal sodium (1.5 g) was added, stirred at the same temperature for one hour and then cooled to room temperature to obtain a solid base (34.9 g).

REFERENCE EXAMPLE 1

To a 200 ml flask, 5-vinyl-2-norbornene (hereinafter referred to as "VNB") (82.5 g) was added under nitrogen. The solid base prepared in Example 1 (0.25 g) was added and stirred at a temperature of 15° to 20° C. for 6 hours.

The solid catalyst was filtered off to obtain a reaction mixture (81.9 g). Gas chromatographic analysis of the mixture revealed that 99.4% of 5-ethylidene-2-norbornene (hereinafter referred to as "ENB") and 0.5% of VNB were contained in the mixture.

EXAMPLE 2

To a 100 ml flask, gamma-alumina (31.9 g) was added and heated to 490°-500° C. under nitrogen with stirring at the same temperature for one hour. After cooling to 300°-310° C., sodium hydroxide (3.0 g) was added thereto and stirred at the same temperature for 3 hours.

Thereafter, metal sodium (1.2 g) and metal potassium (0.3 g) were added, stirred at the same temperature for 30 minutes and then cooled to room temperature to obtain a solid base (33.8 g).

EXAMPLES 3–9 AND COMPARATIVE EXAMPLES 1–2

In the same manner as in Example 1 but carrying out the reaction under the conditions specified in Table 1, a solid base catalyst was prepared.

REFERENCE EXAMPLES 2-11

In the same manner as in Reference Example 1, the solid base prepared in each of Examples 2-9 and Comparative Examples 1-2, VNB was isomerized. The results are shown in Table 2.

(64.5 g) were added and stirred at a temperature of 15°-20° C. for 8 hours. Thereafter, the catalyst was filtered off to obtain a reaction mixture (63.9 g). Gas chromatographic analysis of the mixture revealed that 99.5% of ENB and 0.4% of VNB were contained in the mixture.

TABLE 1

| Example No. | γ-Alumina (g) | Addition conditions of alkali metal hydroxide | | | | Addition conditions of alkali metal | | | | Yield of solid base (g) |
|---|---|---|---|---|---|---|---|---|---|---|
| | | MOH | Amount (g) | Temp. (°C.) | Stirring time (hr) | Alkali metal | Amount (g) | Temp. (°C.) | Stirring time (hr) | |
| 2 | 31.9 | NaOH | 3.0 | 490-500 | 1 | Na.—K | 1.2-0.3 | 490-500 | -5 | 33.8 |
| 3 | 31.9 | NaOH | 3.0 | 390-400 | 1 | Na | 1.35 | 290-300 | 1 | 33.7 |
| 4 | 31.9 | KOH | 3.0 | 340-350 | 3 | K | 1.5 | 200-210 | 1 | 33.2 |
| 5 | 31.9 | NaOH | 3.0 | 310-320 | 3 | K | 1.5 | 240-250 | 1 | 33.7 |
| 6 | 31.9 | NaOH | 3.0 | 310-320 | 3 | Na | 1.5 | 230-240 | 3 | 33.7 |
| 7 | 32.0 | NaOH | 3.0 | 300-310 | 3 | Na | 2.1 | 300-310 | 1 | 33.7 |
| 8 | 31.9 | NaOH | 3.0 | 335-345 | 3 | Na | 1.5 | 335-345 | 1 | 33.6 |
| 9 | 31.9 | NaOH | 3.0 | 300-310 | 3 | Na:K alloy (atomic ratio = 1:1) | 1.5 | 180-190 | 1 | 33.7 |
| Comp. 1 | 31.9 | NaOH | 3.0 | 390-400 | 3 | Na | 1.5 | 390-400 | 1 | 33.8 |
| Comp. 2 | 31.9 | NaOH | 3.0 | 300-310 | 3 | Na | 1.5 | 150-160 | 2 | 33.5 |

TABLE 2

| Reference Example No. | Solid base catalyst | | Amount of VNB (g) | Reaction conditions | | Reaction results | | |
|---|---|---|---|---|---|---|---|---|
| | Example No. | Amount (g) | | Temp. (°C.) | Time (hrs) | Yield (g) | VNB (%) | ENB (%) |
| 2 | 2 | 0.24 | 120 | 15-20 | 6 | 119.7 | 0.6 | 99.8 |
| 3 | 3 | 0.25 | 68.5 | 15-20 | 6 | 68.1 | 0.3 | 99.6 |
| 4 | 4 | 0.25 | 65.5 | 15-20 | 6 | 65.0 | 0.3 | 99.5 |
| 5 | 5 | 0.24 | 61.4 | 15-20 | 6 | 60.9 | 0.3 | 99.2 |
| 6 | 6 | 0.26 | 67.6 | 15-20 | 8 | 67.0 | 1.1 | 98.8 |
| 7 | 7 | 0.24 | 62.6 | 15-20 | 6 | 62.1 | 0.6 | 99.3 |
| 8 | 8 | 0.27 | 54.1 | 15-20 | 6 | 53.7 | 0.3 | 99.6 |
| 9 | 9 | 0.25 | 49.0 | 15-20 | 7 | 48.4 | 0.4 | 99.5 |
| 10 | Comp. Ex. 1 | 0.25 | 39.3 | 15-20 | 8 | 38.8 | 26.0 | 73.9 |
| 11 | Comp. Ex. 2 | 0.25 | 41.8 | 15-20 | 8 | 41.4 | 93.3 | 6.6 |

EXAMPLE 10

To a 100 ml flask, gamma-alumina containing 2.2% by weight of water (30.0 g) was added and heated to 300° C. in a nitrogen stream with stirring at the same temperature for one hour. Metal sodium (1.2 g) was added thereto, stirred at the same temperature for one hour and then cooled to room temperature to obtain a grayish blue solid base (30.9 g).

REFERENCE EXAMPLE 12

To a 200 ml flask in a nitrogen atmosphere, the solid base prepared in Example 10 (0.25 g) and then VNB

EXAMPLES 11-15 AND COMPARATIVE EXAMPLES 3-6

In the same manner as in Example 10 but carrying out the reaction under the conditions specified in Table 3, a solid base was prepared.

REFERENCE EXAMPLES 13-21

In the same manner as in Reference Example 12 but using, as a catalyst, the solid base prepared in each of Examples 11-15 and Comparative Examples 3-6, VNB was isomerized. The results are shown in Table 4.

TABLE 3

| Example No. | γ-Alumina | | Conditions for reacting alkali metal | | | | Solid base prepared | |
|---|---|---|---|---|---|---|---|---|
| | Water content (wt %) | Amount (g) | Alkali metal | Amount (g) | Temp. (°C.) | Stirring time (hr) | Color | Yield (g) |
| 11 | 2.2 | 30.0 | Na:K alloy (Atomic ratio = 1:1) | 1.2 | 200 | 1 | Grayish blue | 31.0 |
| 12 | 2.2 | 30.0 | Na | 1.2 | 350 | 1 | Grayish blue | 30.7 |
| 13 | 3.8 | 30.0 | Na | 2.1 | 310 | 1 | Gray | 31.8 |
| 14 | 2.2 | 30.0 | K | 1.5 | 200 | 1 | Grayish blue | 31.2 |
| 15 | 1.6 | 30.0 | Na | 0.98 | 300 | 1 | Gray | 30.8 |
| Comp. 3 | 2.2 | 30.0 | Na | 1.2 | 150 | 1 | Dark gray | 31.2 |
| Comp. 4 | 2.2 | 30.0 | Na | 1.2 | 400 | 1 | Grayish blue | 30.9 |
| Comp. 5 | 2.2 | 30.0 | Na | 1.8 | 300 | 1 | Dark gray | 31.7 |
| Comp. 6 | 1.4 | 30.0 | Na | 1.35 | 300 | 1 | Dark gray | 31.3 |

TABLE 4

| Reference Example No. | Solid base catalyst Example No. | Solid base catalyst Amount (g) | Amount of VNB (g) | Reaction conditions Temp. (°C.) | Reaction conditions Time (hrs) | Reaction results Yield (g) | Reaction results VNB (%) | Reaction results ENB (%) |
| --- | --- | --- | --- | --- | --- | --- | --- | --- |
| 13 | 11 | 0.24 | 65.3 | 15–20 | 8 | 64.8 | 0.3 | 99.6 |
| 14 | 12 | 0.25 | 50.0 | 15–20 | 8 | 49.7 | 0.5 | 99.4 |
| 15 | 13 | 0.26 | 72.0 | 15–20 | 8 | 71.5 | 0.5 | 99.4 |
| 16 | 14 | 0.24 | 62.4 | 15–20 | 8 | 61.9 | 0.3 | 99.6 |
| 17 | 15 | 0.22 | 47.3 | 15–20 | 8 | 46.9 | 0.5 | 99.4 |
| 18 | Comp. Ex. 3 | 0.24 | 41.5 | 15–20 | 24 | 41.0 | 94.1 | 5.9 |
| 19 | Comp. Ex. 4 | 0.25 | 39.5 | 15–20 | 16 | 38.9 | 57.5 | 42.4 |
| 20 | Comp. Ex. 5 | 0.24 | 50.2 | 15–20 | 16 | 49.7 | 65.4 | 35.6 |
| 21 | Comp. Ex. 6 | 0.24 | 36.7 | 15–20 | 16 | 36.2 | 57.4 | 42.5 |

EXAMPLE 16

To a 100 ml flask alumina comprising gamma-alumina and containing 6.0% by weight of water (50 g) was added and heated to 200° C. with stirring in a nitrogen atmosphere. At the same temperature, metal sodium (4.0 g) was added thereto by portions over 20 minutes. After stirring for one hour, it was gradually heated to 300° C. At said temperature, additional metal sodium (1.9 g) was added thereto by portions over 10 minutes and stirred at the same temperature for 3.5 hours to obtain a solid base (54.2 g).

COMPARATIVE EXAMPLE 7

To a 100 ml flask, alumina comprising gamma-alumina and containing 6.0% by weight of water (50 g) was added and heated to 200° C. with stirring in a nitrogen atmosphere. At the same temperature, metal sodium (4.0 g) was added by portions over 20 minutes. After stirring for one hour, it was gradually heated to 400° C. At said temperature, additional metal sodium (1.9 g) was added by portions over 10 minutes and stirred at the same temperature for 3.5 hours to obtain a solid base (54.1 g).

REFERENCE EXAMPLE 22

To a 200 ml flask in a nitrogen atmosphere, the solid base prepared in Example 16 (0.25 g) and then VNB (62.5 g) were added and stirred at 15°–20° C. for 8 hours.

The solid catalyst was filtered off to obtain a reaction mixture (62.0 g). Gas chromatographic analysis of the mixture revealed that 0.3% of VNB and 99.5% of ENB were contained in the mixture.

REFERENCE EXAMPLE 23

To a 200 ml flask in a nitrogen atmosphere, the solid base prepared in Comparative Example 7 (0.25 g) and then VNB (62.5 g) were added and stirred at 15°–20° C. for 8 hours.

The solid catalyst was filtered off to obtain a reaction mixturre (61.9 g). Gas chromatographic analysis of the mixture revealed that 40.1% of VNB and 59.8% of ENB were contained in the mixture.

REFERENCE EXAMPLE 24

To a 100 ml flask in a nitrogen atmosphere, the solid base prepared in Example 1 (0.21 g) and 2,3-dimethylbutene (99.4% of 2,3-dimethyl-1-butene and 0.6% of 2,3-dimethyl-2-butene (42.0 g) were added and stirred at a temperature of 15°–20° C. for 24 hours to obtain a reaction mixture, which contained 7.7% of 2,3-dimethyl-1-butene and 92.3% of 2,3-dimethyl-2-butene.

REFERENCE EXAMPLE 25

To a 100 ml flask in a nitrogen atmosphere, the solid base prepared in Comparative Example 1 (0.22 g) and 2,3-dimethylbutene (99.4% of 2,3-dimethyl-1-butene and 0.6% of 2,3-dimethyl-2-butene (43.4 g) were added and stirred at a temperature of 15°–20° C. for 24 hours to obtain a reaction mixture, which contained 28.1% of 2,3-dimethyl-1-butene and 71.9% of 2,3-dimethyl-2-butene.

REFERENCE EXAMPLE 26

To a 100 ml flask in a nitrogen atmosphere, the solid base prepared in Example 1 (0.23 g) and 4-methylpentene (98.9% of 4-methyl-1-pentene and 1.1% of 4-methyl-2-pentene) (24.4 g) were added and stirred at a temperature of 15°–20° C. for 16 hours to obtain a reaction mixture, which contained 0.3% of 4-methyl-1-pentene, 10.5% of 4-methyl-2-pentene and 89.1% of 2-methyl-2-pentene.

REFERENCE EXAMPLE 27

To a 100 ml flask in a nitrogen atmosphere, the solid base prepared in Comparative Example 1 (0.24 g) and 4-methylpentene which was the same as used in Reference Example 26 (23.7 g) were added and stirred at a temperature of 15°–20° C. for 120 hours to obtain a reaction mixture, which contained 1.3% of 4-methyl-1-pentene, 45.5% of 4-methyl-2-pentene and 53.2% of 2-methyl-2-pentene.

REFERENCE EXAMPLE 28

To a 100 ml flask in a nitrogen atmosphere, the solid base prepared in Example 10 (0.25 g) and 4-methylpentene (98.9% of 4-methyl-1-pentene and 1.1% of 4-methyl-2-pentene) (22.2 g) were added and stirred at a temperature of 15°–20° C. for 16 hours to obtain a reaction mixture, which contained 0.4% of 4-methyl-1-pentene, 10.8% of 4-methyl-2-pentene and 88.8% of 2-methyl-2-pentene.

REFERENCE EXAMPLE 29

To a 100 ml flask in a nitrogen atmosphere, the solid base prepared in Comparative Example 4 (0.25 g) and 4-methylpentene which was the same as used in Reference Example 28 (22.2 g) were added and stirred at a temperature of 15°–20° C. for 16 hours to obtain a reaction mixture, which contained 1.5% of 4-methyl-1-pentene, 53.2% of 4-methyl-2-pentene and 45.3% of 2-methyl-2-pentene.

What is claimed is:

1. A process for preparing a solid base which comprises reacting alumina with an alkali metal hydroxide in a reaction system at a temperature of from 200° to 500° C. to form a reaction product; adding an alkali metal to the reaction system; and reacting the reaction product with the added alkali metal at a temperature of from 180° to 350° C. or reacting water-containing alumina with an alkali metal in such an amount that corresponds to a molar equivalent of water contained in the alumina in a reaction system at a temperature in a range between the melting point of the alkali metal and 500° C. to form a reaction product; adding an alkali metal to the reaction system; and reacting the reaction product with the added alkali metal in such an amount that the total amount of alkali metal corresponds to 1.01 to 2 times molar equivalent of water contained in the water-containing alumina, at a temperature of from 180° to 350° C., to form the solid base.

2. The process according to claim 1 which comprises reacting alumina with an alkali metal hydroxide in a reaction system at a temperature of from 200° to 500° C. to form a reaction product; adding an alkali metal to the reaction system; and reacting the reaction product with the added alkali metal at a temperature of from 180° to 350° C.

3. The process according to claim 2, wherein alumina and the alkali metal hydroxide are reacted at a temperature of from 250° to 450° C.

4. The process according to claim 2, wherein the reaction product and the added alkali metal are reacted at a temperature of from 200° to 330° C.

5. The process according to claim 2, wherein the alkali metal hydroxide is selected from the group consisting of lithium hydroxide, sodium hydroxide, potassium hydroxide, rubidium hydroxide, cesium hydroxide and mixtures thereof.

6. The process according to claim 2, wherein the alumina is selected from the group consisting of gamma-alumina, chi-alumina, rho-alumina, eta-alumina and mixtures thereof.

7. The process according to claim 6, wherein the alumina is gamma-alumina of 50 to 500 mesh.

8. The process according to claim 1 which comprises reacting water-containing alumina and with an alkali metal in a reaction system at a temperature in a range between the melting point of the alkali metal and 500° C. to form a reaction product; adding an alkali metal to the reaction system; and reacting the reaction product with the added alkali metal at a temperature of from 180° to 350° to form the solid base.

9. The process according to claim 8, wherein the reaction product with an excess molar equivalent amount of the added alkali metal are reacted at a temperature of 200° to 330° C.

10. Th process according to claim 8, wherein the temperature of reacting water-containing alumina with the alkali metal and the temperature of reacting the reaction product with the added alkali metal is at a temperature of 200° to 330° C.

11. The process according to claim 8, wherein the water-containing alumina has been prepared by calcination of aluminum hydroxide, in which the water-containing alumina is selected from water-containing gamma-alumina, chi-alumina, or ro-alumina or eta-alumina.

12. The process according to claim 8, wherein the water content of the water-containing alumina is 1.3 to 10% by weight.

13. The process according to claim 2, wherein the alkali metal and the added alkali metal are each selected from the group consisting of sodium, potassium, rubidium and mixtures and alloys thereof.

14. The process according to claim 8, wherein the alkali metal and added alkali metal are each selected from the group consisting of sodium, potassium, rubidium and mixtures and alloys thereof.

15. The process according to claim 2, wherein the alumina is reacted with the alkali metal hydroxide for a period of 0.5 to 10 hours and the reaction product is reacted with the added alkali metal for a period of 10 to 300 minutes.

16. The process according to claim 12, wherein the water content is 2 to 7%.

* * * * *